(12) United States Patent  (10) Patent No.: US 9,377,288 B2
DeLucia et al.  (45) Date of Patent: Jun. 28, 2016

(54) DENDROMETER

(71) Applicant: Global Change Solutions LLC, Urbana, IL (US)

(72) Inventors: Evan H. DeLucia, Urbana, IL (US); Timothy A. Mies, Urbana, IL (US)

(73) Assignee: GLOBAL CHANGE SOLUTIONS LLC, Urbana, IL (US)

( * ) Notice: Subject to any disclaimer, the term of this patent is extended or adjusted under 35 U.S.C. 154(b) by 56 days.

(21) Appl. No.: 14/298,448

(22) Filed: Jun. 6, 2014

(65) Prior Publication Data

US 2014/0360037 A1  Dec. 11, 2014

Related U.S. Application Data

(60) Provisional application No. 61/832,701, filed on Jun. 7, 2013.

(51) Int. Cl.
G01B 7/12 (2006.01)
G01N 33/00 (2006.01)
G01B 5/00 (2006.01)
G01B 7/16 (2006.01)

(52) U.S. Cl.
CPC ............... *G01B 7/12* (2013.01); *G01B 5/0035* (2013.01); *G01B 7/16* (2013.01); *G01N 33/0098* (2013.01)

(58) Field of Classification Search
CPC .......... G01B 5/0035; G01B 7/16; G01B 7/18; G01B 7/12; G01B 5/025; G01B 7/14
USPC ................ 33/555.4, 555.1, 755–771
See application file for complete search history.

(56) References Cited

U.S. PATENT DOCUMENTS

| | | | | |
|---|---|---|---|---|
| 4,549,355 A * | 10/1985 | Sauer | ...... | A01G 7/00 33/783 |
| 5,406,715 A * | 4/1995 | Koizumi | ...... | G01B 3/1002 33/512 |
| 6,009,631 A * | 1/2000 | Gensler | ...... | G01B 5/0035 33/555.1 |
| 6,185,833 B1 * | 2/2001 | Bravdo | ...... | G01B 7/06 33/783 |
| 6,530,886 B1 * | 3/2003 | Ishida | ...... | A61B 8/0858 600/437 |
| 6,640,460 B1 * | 11/2003 | Nabarro | ...... | A41C 5/00 33/512 |
| 7,146,743 B2 * | 12/2006 | Oura | ...... | A61B 5/107 33/555.4 |
| 7,398,602 B2 * | 7/2008 | Cohen Amar | ...... | G01B 7/18 33/501.6 |
| 2014/0360037 A1 * | 12/2014 | DeLucia | ...... | G01B 7/12 33/555.4 |
| 2015/0116092 A1 * | 4/2015 | Yang | ...... | G01B 5/025 33/555.4 |

* cited by examiner

Primary Examiner — Yaritza Guadalupe-McCall
(74) Attorney, Agent, or Firm — Masuvalley & Partners

(57) ABSTRACT

A dendrometer comprises a dendrometer band whose length is extendable for encircling a tree trunk. The dendrometer further comprises an elongated electronic component that is closely or contiguously attached to the dendrometer band for moving along with the dendrometer band in order to follow length extension of the dendrometer band. Length variation of the dendrometer band is configured to be converted to electronic signals by the electronic component.

31 Claims, 5 Drawing Sheets

DENDROMETER

FIELD OF INVENTION

The present application relates to a dendrometer for measuring diameters or circumferences of tree branches or trunks. The application also relates to methods for making, assembling, installing, configuring, upgrading, repairing, inspecting, dismantling and using the dendrometer. The dendrometer is alternatively known as Band Dendrometer, Tree Hugger™, Tree-Hunger™, TreeHugger™ or Treehugger™, TreeHugger Dendrometer™, TH™ or other similar names.

BACKGROUND OF INVENTION

Dendrometers are metrology or scientific instruments used for measuring various dimensions of trees, such as their diameter, size, shape, age, overall volume and thickness of the bark. One of the most frequently measurements acquired in the field includes DBH (Diameter at Breast Height) of trees. DBH is adopted in estimating the amount of timber volume in a single tree or stand of trees utilizing the allometric correlation between stem diameter, tree height and timber volume. DBH is also employed in estimating the age of veteran trees, given that girth or diameter increment of a tree is the only, constant non-reversible feature of growth. Currently, the two most common dendrometers are a girthing (or diameter) tape and calipers. However, these known instruments often require site visit of personnel to the trees-of-interest, which is costly and tedious for surveying forest tree plots of wide or remote areas.

SUMMARY OF INVENTION

The present invention aims to provide one or more new and useful devices, such as dendrometer. This invention also intends to provide methods for making, assembling, installing, configuring, upgrading, repairing, inspecting, dismantling and using the device. Essential features of the device(s) are provided by independent claims, whilst advantageous features of the device(s) are given by dependent claims. This application claims the priority date of U.S. provisional patent application 61/832,701 that has been filed with USPTO on Jun. 7, 2013. Entire content or subject matter of the earlier priority application is hereby incorporated by reference.

According to a first aspect, the application provides a dendrometer that comprises a dendrometer band whose length is extendable for encircling a tree trunk or tree branch. The dendrometer is also known as band dendrometer, which is often used to measure circumferences/perimeter of tree trunks or sizes of fruits. The dendrometer further comprises an electronic component that is closely or contiguously attached, fixed or adhered to the dendrometer band over a length period for converting length variation of the dendrometer band to electronic signals. Longitudinal extension of the dendrometer band is facilitated by structure of the dendrometer band, which usually has its range beyond elasticity limit of material(s) of the dendrometer band and will not cause irreversible deformation to the dendrometer band. For example, the extension typically is not provided by elastic or plastic behavior of the material(s) of the dendrometer band. In one embodiment, the dendrometer band having two or more stages that provide telescopic extension in its longitudinal direction so that the dendrometer band can hug the tree trunks of various sizes closely or snuggly by extending to suitable length(s). Accordingly, when activated, the electronic component can follow length extension of the dendrometer band and transform length variation or extension movement of the dendrometer band into the analogue or digital electronic signals by the electronic component, such as providing voltage, resistance, inductance and electric current values for indicating the change of tree circumference. In contrast, a foil strain gauge can only operate within its elasticity limit, which merely provides narrow ranges of measurement for dendrometry. Here, the electronic component includes any basic discrete device or physical entity for an electronic system for affecting electrons or their associated fields. The electronic component is usually an industrial product, available in a singular form. Examples of the electronic components contain active components, passive components and electromechanical components.

The dendrometer has simple construction for reliable operation over a prolonged period of time. Since the dendrometer band can be tightened to the tree trunk non-invasively, accurate measurements can be repeatedly taken without interfering growth of the tree trunk. Long range of extension (e.g. 8-2,400 mm if using SoftPot™ potentiometer) permits years of autonomous operation on tree trunks without human intervention for onsite adjustment, calibration or replacement. The dendrometer has flexibility for being mounted onto tree trunks with wide range of circumferences or diameters because the dendrometer band can elongate or shorten itself without reducing its accuracy in measurement. In fact, the dendrometer band can be customized by cutting it to desired length for fitting any designated object (e.g. tree branch or fruit). Since materials or parts of the dendrometer band and the electronic component are readily available in the market at low cost (e.g. SoftPot™ potentiometer), the dendrometer can be sold at affordable prices, benefiting dendrometry application of dispersed or wide areas of forests or plantations.

The electronic component can comprise a passive electronic component that includes switch, resistor, capacitor, inductor, transformer, memristor, (RC or LC) network of passive components, transducers, sensors, detectors, antenna, assembly/module (e.g. oscillator, digital voltmeter) and prototyping aids (e.g. wire-wrap, breadboard). In contrast, the active electronic components include semiconductor (e.g. diode, LED), transistor (e.g. thyristor), integrated circuit (digital or analogue), optoelectronic device, light-emitting device (e.g. filament lamp, nixide tube), vacuum tube, optical detector or emitter, and power source (e.g. battery, fuel cell). Since some of the passive electronic components can be made into different forms (e.g. film or sheet) cheaply, the passive electronic component can be fixed onto the dendrometer band in order to follow or capture linear/longitudinal extension of the dendrometer band. For example, an array of switches can be printed onto the dendrometer band such that electrical connection of one or more of the switches provides extent of the linear/longitudinal extension. Electricity consumption of the dendrometer can possibly be greatly reduced for prolonged autonomous operation of the dendrometer because the passive electronic component only consumes electricity when in operation (e.g. taking periodic reading), not necessarily in standby mode.

The passive electronic component may comprise a potentiometer, variable resistor or rheostat. The potentiometer typically comprises a resistive element and a sliding contact (wiper) that moves along the resistive element for making good electrical contact. For example, Sparkfun™ (distributor) and Spectra Symbol™ in Salt Lake City, Utah (manufacturer) of USA provide SoftPot™ Membrane Potentiometers whose resistance values linearly change from 100 Ohms to 10,000 Ohms, allowing very accurate calculation of relative positions on the Membrane Potentiometers. The potentiometer (alternatively known as membrane potentiometer or membrane switch) comprises a collector, a circuit spacer, a bus bar (resistor), resistor and a bottom adhesive that are sequentially stacked and packaged. Since the potentiometer is sealed against harsh environments, the dendrometer may be made to withstand diverse types of weather conditions. When using a SoftPot™ Membrane Potentiometer of 500 mm active area length, the dendrometer band can measure circumference change of the tree trunk up to 0.5 meter, which is a very long period of growth and observation for trees. Membrane potentiometers may be further customized such that active lengths of the membrane potentiometers can be made from several millimeters to more than a few meters from specific applications or trees. The potentiometer can provide high accuracy of measurement to tree trunks, typically within 10 μm. When in use, the potentiometer can enable the dendrometer to measure changes of circumference of a tree trunk with a resolution of ±6 μm at ≥1 min sampling interval.

The dendrometer band can comprise a circuit band for carrying one or more parts of the electronic component, and a plunger band for carrying one or more other parts of the electronic component, such as a plunger/wiper of the potentiometer. The circuit band and the plunger band are configured to cooperate with each other moveably in for sliding in longitudinal directions of the two bands. The two bands may also be partially fixed to each other for providing the electronic signals (e.g. voltage, current). For example, the circuit band includes the collector, the circuit spacer, the bus bars and the resistor that are adhered to a stainless steel band by permanent glue. The wiper or plunger can be mounted (e.g. spring-loaded or spring-plate attached) to a plastic stripe in forming the plunger band. The circuit band and the plunger band may be guided with respect to each other by rails, slots or casings such that the two bands can closely attach to each other and move in their longitudinal directions for achieving telescopic motion (length variation). Of course, parts of the electronic component (e.g. membrane potentiometer) may be exchanged in their position on the two bands depending on requirements. Any of the two bands can be made with lightweight materials, and they can be cut to desired sizes onsite (e.g. near a tree trunk) for customization.

Preferably, the circuit band, the plunger band, or any parts of the two bands comprise one or more stainless steel (i.e. inox steel) stripes. Since stainless steel material requires little maintenance and can be recycled, life span of the dendrometer is dramatically prolonged, compared to known dendrometers. One way of recycling a stainless steel stripe is to connect its two opposite ends to a dendrometer band so that the dendrometer can measure a trunk with larger circumference.

In one embodiment, the plunger band comprises a stainless ribbon for mounting a plunger of the potentiometer. Since the stainless steel ribbon provides a wide and robust base for mounting onto a trunk, the plunger band has long-term reliability and durability for operation.

In another embodiment, the dendrometer band comprises a clip for guiding movement of the circuit band, the plunger band or both. The clip may be in the form of sheet metal folded around one of the bands so that another band can slide within the clip. The clip can be integrally or separately formed on either one of the bands. The clip may further be fixed onto any of the two bands. When in use, the clip prevents the wiper/plunger from working outside active area of the potentiometer.

The dendrometer band may comprise a stopper (e.g. by welding) for limiting longitudinal movement of the circuit band, the plunger band or both. When using membrane potentiometer, the stopper constrains the wiper/plunger to slide within the active area so that the dendrometer can provide proportional change of potential/resistance depending length variation/extension of the dendrometer. The stopper may be in the form of a stud, a bent-stripe, a rivet, a block or a spring. The stopper may be detachable so that the stopper can be relocated after changing the electronic component (e.g. membrane potentiometer).

The dendrometer band can further comprise a spring for connecting the circuit band and the plunger band by opposite ends of the spring. The spring is alternatively known as an elastic object used to store mechanical energy. Known examples of the spring include tension/extension spring (based on type of force) or coil spring (based on shape). For example, one end of the spring is detachably linked to a hook on the circuit band, whilst another end of the spring is removably joined to an orifice on the plunger band. Resilient force of the spring makes the dendrometer band to contract/reduce to its minimum length, thus hugging the tree trunk tightly. Hence, the spring ensures that the dendrometer band encircles the tree trunk tightly and snuggly, without losing accuracy due to thermal expansion or contraction of the dendrometer band. Thus, the dendrometer is able to capture a wealth of data relating to short range of contraction and expansion of tree trunks, which are not visible to the naked eye. For example, stems of trees shrink and expand daily in the range of several millimeters due to water circulation in leaves and roots of the trees. The spring enables the dendrometer to follow both expansion and contraction of tree trunks generated by the evaporative demand of the leaves and water supply rate to tree roots. The spring may be replaced by one or more multiple resilient means or extendable devices, such as helical springs, rubber bands, magnetic spring, gas spring, hydraulic spring and bows.

In a further embodiment, the dendrometer band, the electronic component or both devices are at least partially weatherproof, scratchproof, dustproof, shockproof or having a combination of any of these properties. Dendrometers are often deployed and unattended in forests for long periods of time (e.g. nine months), these components enables the dendrometer to provide consistent performance without site-visit by researchers, engineers or technicians, thus achieving cost and time savings.

The dendrometer band, the electronic component or both articles are protected against external intrusion of solid particles, liquid ingress, mechanical impact, electric shock or a combination of any of these. For example, the electronic component (e.g. potentiometer) has IP65 (International Protection Marking) prevents ingress of dust and water splashing. These components may be further enhanced for preventing influence of various weather conditions (e.g. snowing) and mechanical impacts (e.g. squirrel scratching).

In one embedment, the dendrometer has a data logger that is connected to the electronic component for reading the electronic signals. The data logger may include microprocessor(s), solid state memory, RAM (Random Access Memory), battery, PCB (printed Circuit Board), integrated circuit(s), LED (Light Emitting Diode), antenna(s), user interface(s) and other electronic components for data processing and transmission. The data logger may process and store data locally at the solid state memory (e.g. Secure Digital Cards as non-volatile memory cards), or transmit the data to a central location (e.g. a remote station). The data logger may be loaded with an operating system and one or more application software packages such that the data logger can communicate with a computer or a mobile computing device (e.g. tablet computer).

Another embodiment of the dendrometer further comprises an electric cable for connecting the electronic component to the data logger. The electric cable may have connectors (e.g. type 0L, 1E or 0F, crimp connectors) that allow detachment or connections between the data logger and the dendrometer band conveniently.

The dendrometer or the data logger may comprise an electrical energy source (e.g. energy harvesting device, energy storage device) for powering the data logger. The energy source provides electricity to the data logger to periodically record data from the dendrometer band for future analysis of one tree or data analytics of many trees. When one or more energy harvesting devices are deployed, the dendrometer can operate autonomously such that a researcher does not have travel to the dendrometer physically for servicing. When required, the dendrometer can send an alert message/signal to a user for servicing when required.

The data logger can further comprise a memory device (e.g. hard disk drive or memory stick) for data storage or processing locally. Since modern memory devices are cheaply available, one data logger or dendrometer can record and store data for multiple dendrometers or other forest monitoring devices within its vicinity.

In an embodiment, the data logger or the dendrometer further comprises an antenna (aerial) for radio/wireless signal transmission or reception. The antenna enables digital or analogue communication of the data logger such that the data logger or the dendrometer may be remotely or wirelessly accessed, configured, repaired and upgraded. The dendrometer or data logger may even be internet or satellite accessible. The data logger may include a ZigBee module based on IEEE802.15 standard such that the data logger can provide long battery life and secure networking with low data rate. The data logger may incorporate telecommunication modules for connecting 3G network (Universal Mobile Telecommunications System) such that the dendrometer can be deployed over a wide and remote area by using existing telecommunication networks.

In a further embedment, the dendrometer band, the electronic component or both comprises markings or inscription for visualizing the length variation. The markings or inscription allows convention metrology tools (e.g. caliper, micrometer) or human visual readings (e.g. with magnifying glass) when calibrating the dendrometer.

In another embodiment, the dendrometer comprises a data logger that has low cost and low power consumption. High resolution or high accuracy of the dendrometer may not be compromised by the low cost because market price of the electronic component (e.g. potentiometer) is only about US $12.95 currently when buying individually. The dendrometer may include one or more temperature sensors (e.g. thermistor or thermocouple) for measuring local temperature of the dendrometer band so that thermal expansion of the dendrometer band can be compensated by electronic circuit(s) or software program(s) of the data logger. The data logger can include one or more analogue-to-digital converters for converting analogue signals from the electronic component to digital signals for further processing. Examples of analogue-to-digital semiconductor chips include NAU7802 of NuvoTon Technology, AD7705 of Analogue Devices and MCP3424 of Microchips.

The present application also provides one or more sensor networks that comprise the dendrometer and a gateway sensor node wirelessly connected or cable-connected to the dendrometer. The sensor network(s) can monitor wide variety indicators of a forest so that regulatory authorities and/or research institutions can obtain real-time data for managing forests, combating climate change.

The application further provides a wireless sensor network that comprises the sensor network and one or more radio transceivers having one or more antennas for communication between the dendrometer, the gateway sensor node or other computing devices. One or more of the wired or wireless sensor network may be inter-connected for county-wide, state-wide or nation-wide monitoring. The wireless sensor network can greatly reduce cost of monitoring, providing real-time information to interested parties.

According to a second aspect, the application provides a method for using a dendrometer. The method comprises a step of clasping or encircling the dendrometer onto a tree trunk such that the dendrometer can extend its length following circumference growth of (i.e. around) the tree trunk. The method further comprises a step of powering (e.g. providing 2.56 volt DC to) the dendrometer for generating and/or receiving electronic signals. The method also comprises a step of converting the electronic signals to circumference growth data of the tree trunk. Any of these method steps described by the present application may be altered in sequence depending requirements or suitability. The dendrometer can be intuitively used by a technician according to these few steps. A person who has prior experience of using other types of dendrometer will find the dendrometer simple to operate.

The method may further comprise a step of electrically connecting an electronic component of the dendrometer to a data logger for data processing locally. The data logger can be used to configure, calibrate and monitor performance of the dendrometer after making the electrical connection.

The method can further comprise a step of transmitting the electronic signals to another electronic device. In other words, two or more electronic devices begin to "talk" (communicate) to each other such that the dendrometer can operate independently or within a network.

According to a third aspect, the application provides a method for installing a dendrometer. The method comprises a step of providing a dendrometer band that has a circuit band, a plunger band and a clip for guiding movement of the circuit band, the plunger band or both. The method also comprises a step of encircling the dendrometer band around a tree trunk and a step of joining the circuit band and the plunger band by a spring or other elastic means for clasping the tree trunk. Since the installation can be completed by using a hand tool or with free hands, the dendrometer can be attached to a tree trunk easily and reliably. Tedious procedure of adjustment and numerous spare parts are avoided.

According to a fourth aspect, the present application provides a method for servicing a dendrometer. The method comprises a step of cleaning or adjusting a dendrometer band for giving sufficient range of extension to the dendrometer band. For example, if a SoftPot membrane potentiometer of 500.00 mm (19.685") is adopted, a plunger/wiper on a plunger band is positioned within the 10 mm at a beginning range of a circuit band after the servicing. Providing the plunger or wiper at the beginning portion of the measuring range maximizes measuring capacity of the dendrometer. Careful cleaning or adjusting of the dendrometer will provide added life span to the dendrometer without incurring much cost and effort.

The method for servicing the dendrometer can comprise a step of replacing faulty parts of the dendrometer band. Once repaired, the dendrometer resumes its normal operation without additional cost. The component replacement also includes change of batteries or rusty parts. The method of servicing may further include a step of attach or adhere another membrane potentiometer to the dendrometer band to prolong life of the dendrometer. The method of servicing can also include a step of lengthening the dendrometer band by patching another band.

According to a fifth aspect, the application provides a method for configuring a dendrometer. The method comprises a step of providing a dendrometer band with a circuit band and a plunger band. The application also includes another step of examining range of movements of the circuit band and the plunger band. The method includes a third step of adjusting lengths of the circuit band, the plunger band or both for providing sufficient operation range to an electronic component of the dendrometer when clasping a tree trunk. This method effectively extends useful lifespan of the dendrometer.

According to a sixth aspect, the application provides a method for making a dendrometer. The method comprises a step of providing a dendrometer band, a step of attaching an electronic component to the dendrometer band for generating electronic signals when extending the dendrometer band, and a step of connecting leads of the electronic component to a cable. The dendrometer can be made with little time and cost, thus benefiting a large pool of users.

The method of making further comprises a step of presenting a data logger for receiving the electronic signals. The data logger can convert electronic signals to meaningful data for tree growth monitoring. The data logger may be supplied by manufacturers of the dendrometer, or users themselves by configuring existing available data logger(s).

According to a seventh aspect of the invention, the present application provides a dendrometer that comprises a main belt for attaching to a tree trunk, a secondary belt having a first end fixed onto to the main belt and a second end movable with respect to the main belt; and a spring that is connected between the main belt and the secondary belt for pulling the secondary belt to the main belt. The main belt and the secondary belt are flexible or resilient for wrapping around the tree trunk in order to measure the girth of a tree. The main belt can comprise a folded end that has slots for guiding movement of the secondary belt along the main belt. The dendrometer may further comprise a plunger sensor on the main belt for measuring a distance between the main belt and the tree trunk. The dendrometer can further comprise a SoftPot sensor on the secondary belt for gauging relative movement between the main belt and the second belt. The plunger sensor, the sensor, or both may have ingress protection against water or dirt. The SoftPot sensor can comprise an elongated datable region for determining the change of length with a predetermined range. The dendrometer may further comprise an electronic circuit that is connected to the plunger sensor, the SoftPot sensor or both sensors for taking measurement locally. The electronic circuit can further comprise a data storage device for storing measured data locally. The electronic circuit may further comprise a microprocessor for data processing locally. The electronic circuit can further comprise an antenna for wireless communication. The electronic circuit may further comprise an energy storage device for powering the electronic circuit. The electronic circuit can further comprise a network interface for data communication with another dendrometer or a remote work station. The electronic circuit further may comprise a casing for protecting the electronic circuit against external disturbance. The electronic circuit can further comprises a linear potentiometer configured as a voltage divider within the Softpot sensor to provide a linear voltage signal relative to the plunger position along the length of the SoftPot. The main belt, the secondary belt, the spring or all of them may be made of stainless material, which has a low thermal coefficient and provides a low friction surface against the tree.

According to an eighth aspect of the present invention, the application provides a method of using a dendrometer. The method comprises a first step of providing a main belt for attaching to a tree trunk; a second step of supplying a secondary belt having a first end and a second end; a third step of fixing the first end onto to the main belt and allowing the second end to be movable with respect to the main belt; a fourth step of wrapping the main belt and the secondary belt around the tree trunk for measuring girth of a tree and a fifth step of connecting a spring between the main belt and the secondary belt for pulling the secondary belt to the main belt. Some of these steps may be changed in sequence for achieving similar results.

BRIEF DESCRIPTION OF DRAWINGS

The accompanying figures (Figs.) illustrate one or more embodiments, and serve to explain principles of the disclosed embodiment(s). It is to be understood, however, that these figures are presented for the purpose of illustration only, and not for defining limits of relevant inventions. Exemplary, non-limiting embodiment(s) of the present invention will now be described with reference to the above-mentioned figures.

DETAILED DESCRIPTION

Figure 1:
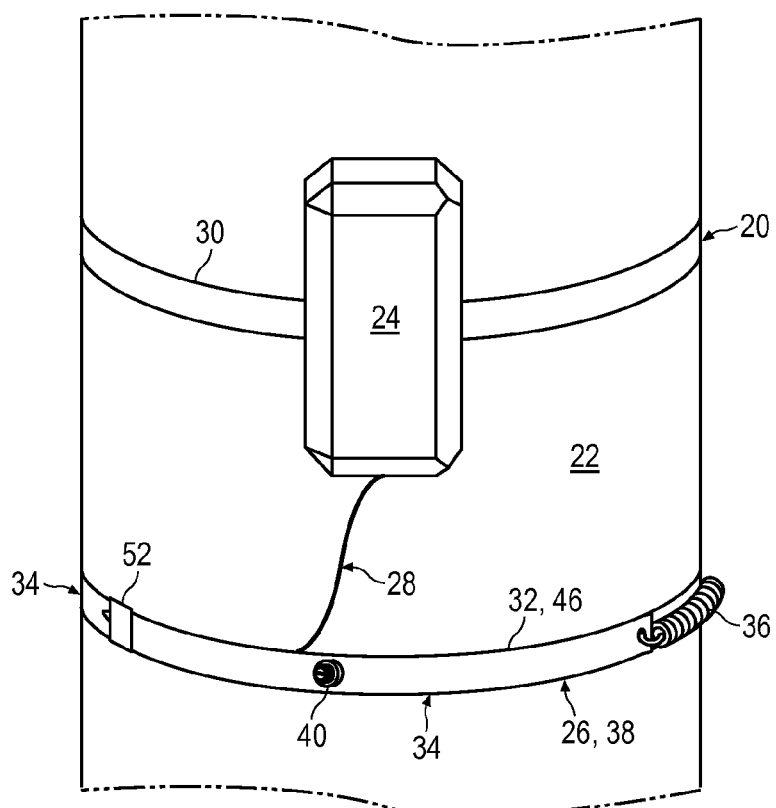
FIG. 1 illustrates a dendrometer that is installed on a tree trunk.

FIGS. 1-8 provide an embodiment of the present invention. Parts of the embodiment are labeled by identical or similar reference numerals. Description that corresponds to the identical or similar reference numerals is hereby incorporated by reference, wherever relevant or appropriate.

Figure 2:
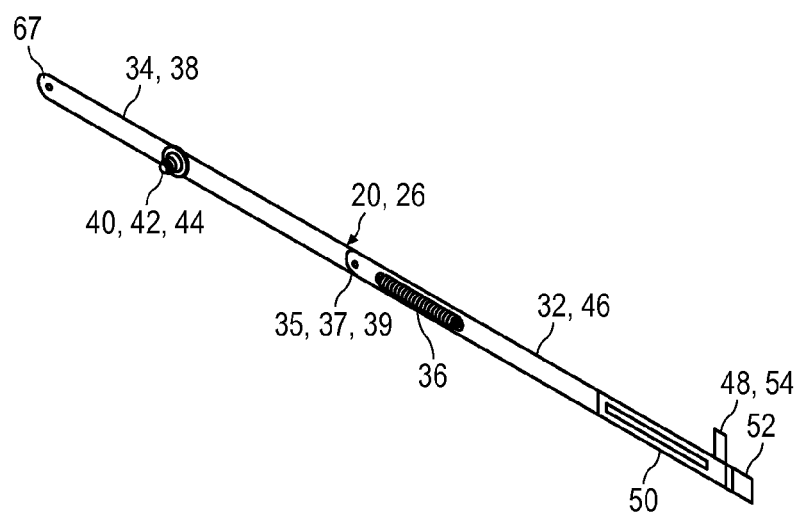
FIG. 2 illustrates bands of the dendrometer that are extended in their longitudinal directions.

Particularly, FIG. 1 illustrates a dendrometer 20 that is installed on a tree trunk 22. The dendrometer 20 comprises a data logger 24 and a dendrometer band 26 that are connected via a cable 28. The data logger 24 is mounted onto the tree trunk 22 via a stainless belt 30, which wraps around the tree trunk 22. The dendrometer band 26 includes a circuit band 32 and a plunger band 34 that are closely attached and overlap partially. A first end 35 of the circuit band 32 and a first end 37 of the plunger band 34 are connected by a first rivet 39 such that they are serially connected, as shown in FIG. 2. The dendrometer band 26 further comprises a spring 36 whose opposite ends are connected to the circuit band 32 and the plunger band 34 respectively.

FIG. 2 illustrates the bands 32, 34 of the dendrometer band 26 that are extended in their longitudinal directions. The plunger band 34 has a stainless steel strip (i.e. ribbon or belt) 38 and a plunger 40. The stainless steel strip 38 has a width of 20 mm (millimeter), a length of about 450 mm and a thickness of 0.5 mm. The plunger 40 includes a standard wiper 42 and a cylindrical casing 44 such that the standard wiper 42 is inserted into the cylindrical casing 44, and they 42, 44 are both perpendicular to a broad surface (length versus width) of the plunger band 34. The standard wiper 42 is spring-loaded via a screw (not shown) in the cylindrical casing 44.

The circuit band 32 includes a stainless steel ribbon (i.e. belt or strip) 46, an anchoring tag 48, a membrane potentiometer 50 and a clip 52. The stainless ribbon 46 has a width of 20 mm (millimeter), a length of about 520 mm and a thickness of 0.5 mm. The anchoring tag 48 is a riveted fixture with an extension ring (not shown) and a thermistor 68. The membrane potentiometer 50 is a SoftPot™ Membrane Potentiometer of 200 mm length (SEN-08679 RoHS), which is provided by Spectra Symbol of Salt Lake City, Utah 84119, USA. The membrane potentiometer 50 may be simply known as potentiometer, variable resistor or rheostat. Both the thermistor 68 and the membrane potentiometer 50 are connected to the data logger 24 via the cable 28. The clip 52 is a folded stainless strip, and the clip 52 is fixed to the end of the circuit band 32. The clip 52 further provides a slot 59 such that the plunger band 34 can slide within the clip 52 for extending length of the dendrometer band 26. The membrane potentiometer 50 is adhered to a broad side (length versus width) of the stainless steel ribbon 46, and mutually aligned in their longitudinal directions. The membrane potentiometer 50 comprises a connector 54, which is a Crimpflex solder tab for attachment of the cable 28.

Figure 3:
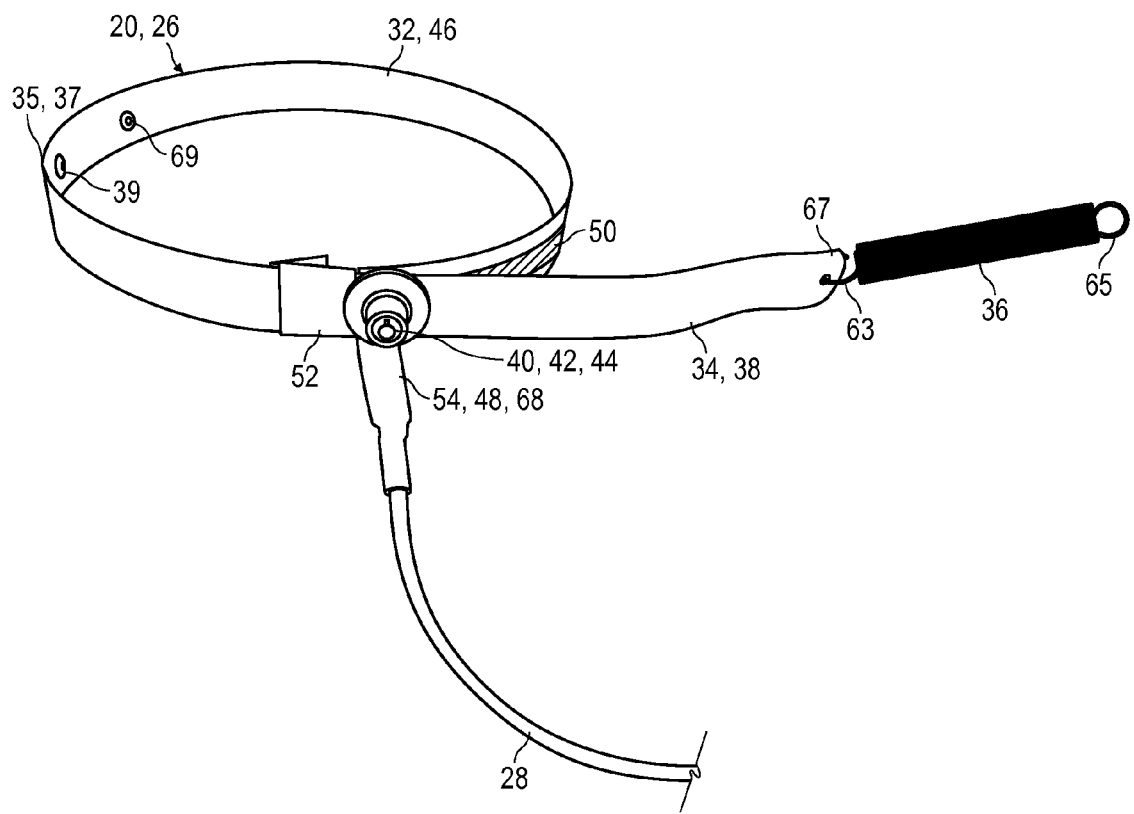
FIG. 3 illustrates the dendrometer band as assembled, but not mounted onto the tree trunk.

FIG. 3 illustrates the dendrometer band 26 as assembled, but not mounted onto the tree trunk 22. In this form, the plunger band 34 has been serially connected to the circuit band 32 by the first rivet 39 such that they 34, 32 form an elongated ribbon or belt. The plunger band 34 is further inserted through the gap 59 on the clip 52 that is fixed to an end of the circuit band 32. Respective movement between plunger band 34 and the circuit band 32 is limited by the clip 52 and the plunger 40 because the plunger 40 cannot move beyond the clip 52.

The spring 36 has two ends that are at opposite ends, consisting of a plunger end 63 and a circuit end 65. The plunger end 63 is hooked to an end 67 of the plunger band 34, whilst the circuit end 65 is to be joined to a riveted tag 69 (not visible) on the circuit band 65. Of course, when installing the dendrometer band 26 in the field (e.g. forest plantation), the first rivet 39 may be only connected after adjusting and mounting the spring 36.

Figure 4:
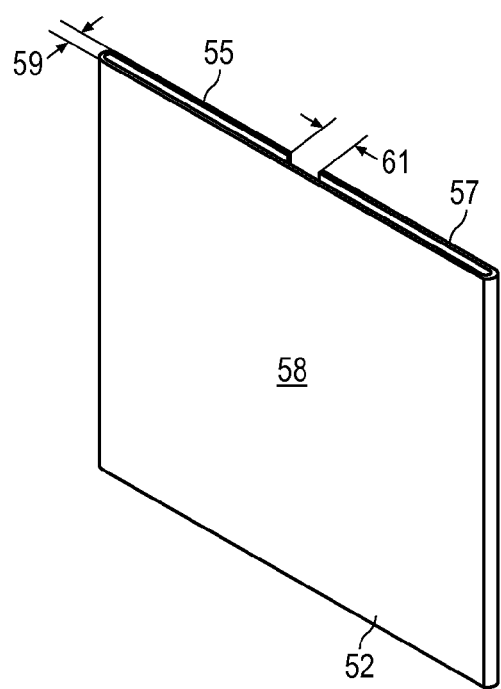
FIG. 4 illustrates a clip of the dendrometer.

FIG. 4 illustrates the clip 52 of the dendrometer 20. The clip 52 is made from a single stainless steel sheet, which is folded with two wings 55, 57. The clip 52 has a base 58 that is substantially parallel to the two wings 54, 56 respectively. A first wing 55 and a second wing 57 have a gap 61 of 5 mm in-between them throughout a length of the clip 52 (in a vertical direction of FIG. 4). Furthermore, each of the first wing 55 and the second wing 57 are detached from the base 58, creating the slit 59 of 0.6 mm for receiving and sliding plunger band 34.

Figure 5:
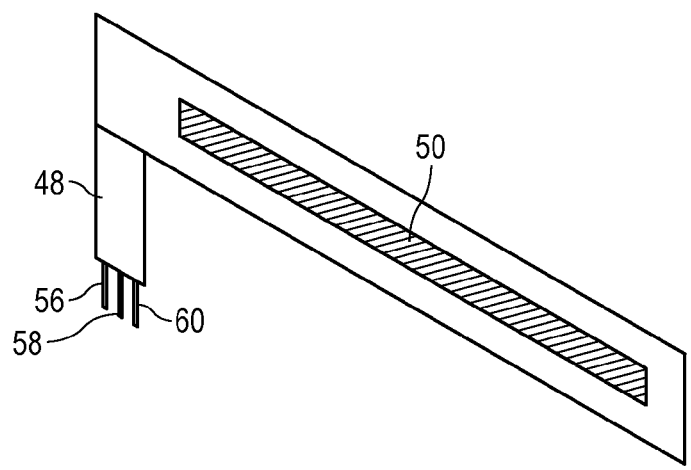
FIG. 5 illustrates a membrane potentiometer of the dendrometer.

FIG. 5 illustrates the membrane potentiometer 50 of the dendrometer 20. The membrane potentiometer 50 is a resistive element, which comprises a conductive resistor (bottom circuit and top circuit), a sealed encasement and a simple wiper 42 assembly. The membrane potentiometer 50 can also function as a voltage divider. In use, by pressing the standard wiper 42 down onto a top circuit, the membrane potentiometer 50 produces desired electrical output. The standard wiper 42 is a non-conductive mechanism that depresses the top circuit actuating the membrane potentiometer 50 from the outside of the circuits. The top and bottom circuits are separated by 0.15 mm (0.006") of spacer adhesive build-up and contact between the circuits occurs by pressure (usually 1 to 3 Newton) from the wiper 42 on the top circuit, pushing down until the top circuit connects with the bottom circuit for creating an electrical potentiometric output. The membrane potentiometer 50 has a three-wire system with two resistive output channels and an electrical collector channel. The electrical collector channel is activated by the standard wiper 42 when pressed again the top circuit and bottom circuit. In FIG. 5, three electrical leads of the connector 54 are exposed, which consist of Pin A (i.e. Pin 1 connected to bottom bus bar, V+) 56 for receiving positive voltage potential, Pin B (Pin 2) 58 as input pin for connecting to the collector or plunger 40 and Pin C (Pin 3) 60 for joining the Ground potential (GND) or top bus bar. The potentiometer 50 generally has several layers that are sequentially attached together, which includes bottom adhesive layer, bus bar(s), resistor, circuit spacer and collector.

Figure 6:
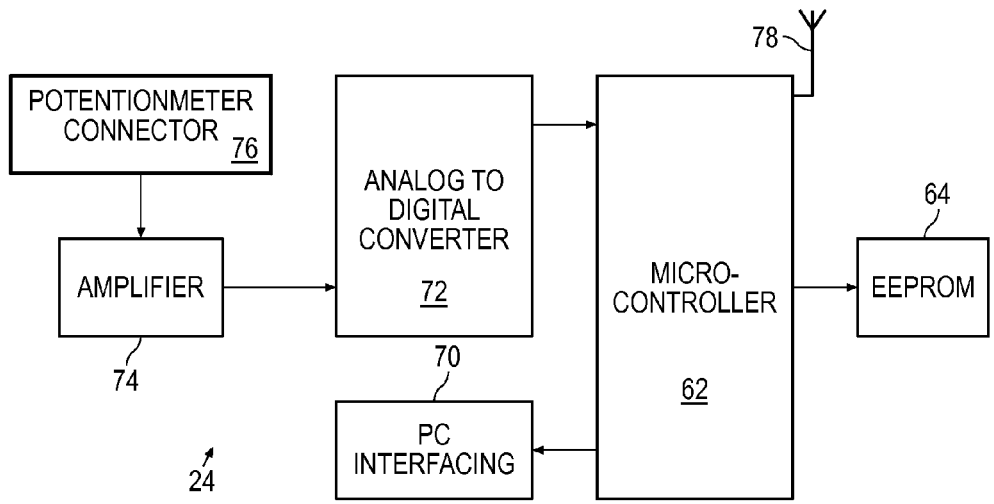
FIG. 6 illustrates a schematic diagram of a data logger for the potentiometer.

FIG. 6 illustrates a schematic diagram of the data logger 24 for the potentiometer 50. The data logger 24 has a microcontroller (microprocessor) 62, an EEPROM (Electrically Erasable Programmable Read-Only Memory) 64, a PC (personal computer) interface 70, an Analog-to-Digital Converter 72, an amplifier 74, a potentiometer connector 76 and an antenna 78. The EEPROM 64, the Analog-to-Digital Converter 72 and the PC interface are connected to the microcontroller 62 such that preloaded operating system and data logging application software package can operate automatically for data collection and transmission. The potentiometer connector 76 is connected to the Analog-to-Digital Converter 72 via the amplifier 74 such that minor voltage signals can be augmented and filtered for processing by the microcontroller 62. The antenna 78 (aerial) is connected to the microcontroller 62 for providing wireless communication by a data logger application software package.

Figure 7:
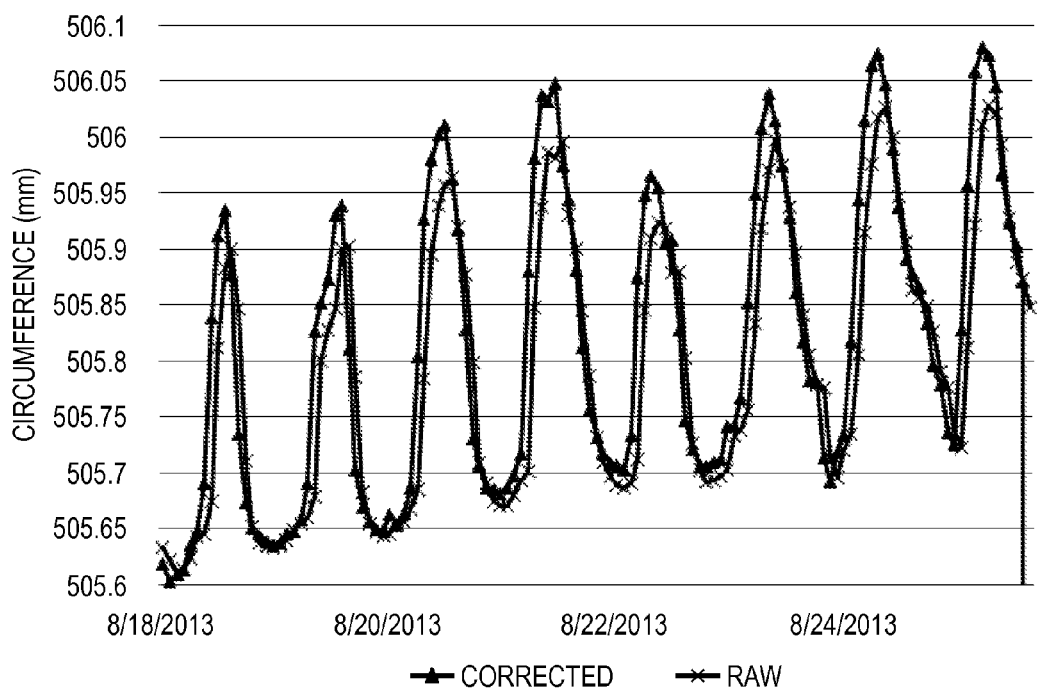
FIG. 7 illustrates measurement results of the tree trunk over one month by using the dendrometer.

FIG. 7 illustrates measurement results of the tree trunk over one month period by using the dendrometer 20. The tree trunk belongs to a sugar maple tree in central Illinois State, which is measured by the dendrometer band (TreeHugger™) with onboard data storage (SD card). Raw data (orange colored) have been illustrated together with temperature-corrected (thermal expansion compensated) data (blue colored). These data correspond very well with manually obtained data by using a Vernier Caliper.

FIG. 7 indicates that the dendrometer 20 is able to capture circumference variation of the tree trunk 22 over a relatively short period automatically. Data of FIG. 7 clearly indicates the consistent growth rate of the tree trunk 22 at about 0.076 mm/day, which is otherwise not discernable by conventional manual measurement technique. Reliable, accurate and real-time data of tree growth will greatly facilitate tree cultivation and forest plantation. In fact, the dendrometer 20 is so accurate that measurement data of the dendrometer 20 are subjected to temperature variations of its ambient environment.

Effect of thermal expansion and contraction on the dendrometer band 26 has been calibrated for further improvement of measurement accuracy. The effect of thermal expansion has been calculated according to following equation:

$$\Delta X = L * \Delta T * C_{TE} \quad \text{(Equation A)}$$

Where
$\Delta x$ means the change in length;
L means the length of material;
$\Delta T$ means the change in temperature (degree Celsius); and
$C_{TE}$ means the coefficient of thermal expansion.

Since the membrane potentiometer 50 is adhered to the stainless steel ribbon 46 by a strong adhesive backing of 3M™, the adhered membrane potentiometer 50 has the coefficient of thermal expansion ($C_{TE}$) of about 14.82 μm/m° C. (micrometers per meter per degree Celsius). In contrast, an un-mounted (non-installed) membrane potentiometer 50 has the coefficient of thermal expansion ($C_{TE}$) of about 23.29 μm/m° C. In other words, thermal expansion of the membrane potentiometer 50 has been adapted to the thermal expansion of the stainless steel ribbon 46 after assembling or installation.

Compensation of thermal expansion to the dendrometer band 26 is calculated by taking reference from a base point, which is provided by using Equation B (see below). This base point provides the reference for the change in temperature. The change in temperature is multiplied by the previous recorded diameter of the trunk 22 and the coefficient of thermal expansion.

$$\Delta X = D_L(T-T_B) * C_{TE} \quad \text{(Equation B)}$$

$$\Delta T = T - T_B \quad \text{(Equation C)}$$

Where:
Δx means the change in length;
$D_L$ means the previously recorded diameter of the trunk;
T means temperature value (degree Celsius) of the recording of interest;
$T_B$ means temperature value (degree Celsius) of the previous recording as reference (base point); and
$C_{TE}$ means the coefficient of thermal expansion.

According to experimental results by using above-mentioned equations, the coefficient of thermal expansion for the membrane potentiometer 50 is 23.29 μm/° C., the coefficient of thermal expansion for the adhered/assembled the membrane potentiometer 50 on the circuit band 32 is about 14.82 μm/° C. Since the coefficient of thermal expansion for the stainless steel banding is about 14.83 μm/° C., the coefficient of stainless steel can be used for the thermal expansion correction Equations A~C without affecting measurement accuracy.

Figure 8:
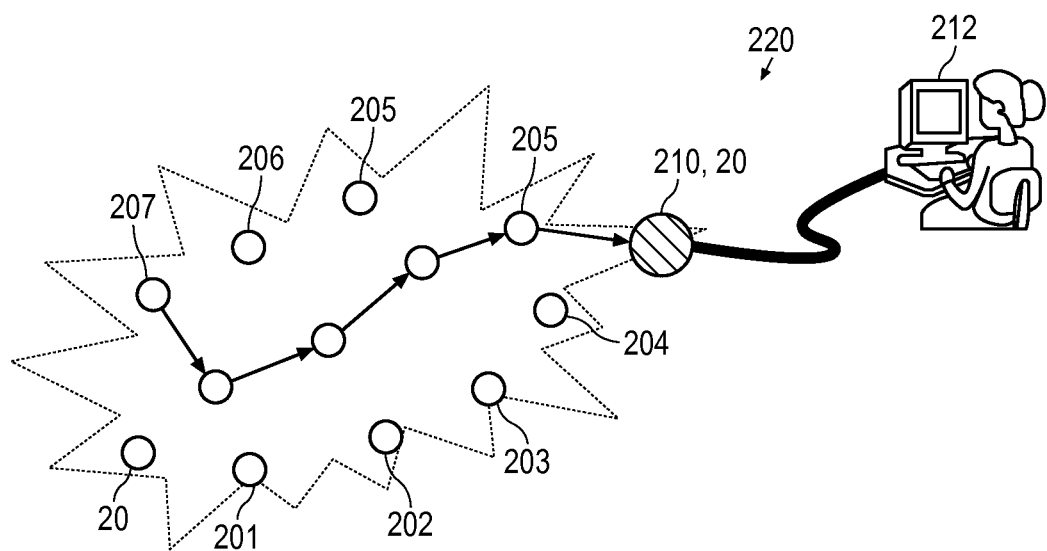
FIG. 8 illustrates a sensor network that utilizes the dendrometer.

FIG. 8 illustrates a sensor network 220 that utilizes the dendrometer 20. The sensor network 220 comprises sensor nodes 20, 201-207, a gateway node 210, 20 and base station 212. Each of the sensor nodes 20, 201-207 and the gateway node 210, 20 comprises a radio transceiver with an internal antenna or connection to an external antenna, a microcontroller, an electronic circuit for interfacing with the sensors and an energy source, usually a battery or an embedded form of energy harvesting, which are not shown. The base station 212 is connected to these nodes 20, 201-207. 210 via one or more forms of low energy wireless network (e.g. ZigBee based on IEEE 802.15 standard) such that the base station 212 can obtain real-time data of tree trunk growth and configure these nodes in response to temperature (e.g. due to season change).

[Method of Use]

In use, bark of the trunk 22 is trimmed for providing two parallel narrow strips of relatively smooth surface around the trunk 22. Inner bark of the trunk 22 is prevented from the trimming so that normal growth of the trunk 22 is not affected by the trimming. In other words, living tissue of the trunk 22 is not affected by the trimming.

For installation, the plunger band 34, the circuit band 32 and the data logger 24 are taken to the trunk 22 for installation. The plunger 40 is readily fitted onto the plunger band 34. A free end 67 of the plunger band 34 is inserted into the clip 52 such that the plunger band 34 can slide along the circuit band 32. Two opposite ends 63, 65 of the stainless spring 36 are hooked to the free end 67 and the rivet tag 69 such that the plunger band 34 and the circuit band 32 are linked together in forming a single long belt 26.

The single long belt 26 is wrapped around the trunk 22 such that overlapped parts (not shown) of the two bands 32, 34 are marked out. The overlapped parts are trimmed off, leaving sufficient portions for riveting the two bands 32, 34 together. The stainless spring 36 may be taken off when trimming the bands 32, 34 for convenience. Particularly, the standard wiper 42 is located with 10% of the beginning portion of the membrane potentiometer 50 when marking and trimming the overlapped parts. After riveting the two ends 35, 37, the two opposite ends 63, 65 of the stainless steel spring 36 are hooked back to the dendrometer band 26 at the end of the plunger band 67 and the riveted tag 69 on the circuit band 32.

The stainless steel belt 30 is inserted through a mounting slot (not shown) of the data logger 24. The stainless steel belt 30 is tied around the trunk 22 such that the data logger 24 is slight above and adjacent to the plunger 40. The connector 54, which is at the end of the cable 28, is plugged into the data logger 24 such that electrical connection is established between data logger 24 and the dendrometer band 26.

For data logging, the data logger 24 is switched on so that application software of the dendrometer 20 starts to operate. The data logger 24 comprises a lithium battery (not shown), a temperature sensor (thermocouple), a circuit board (not shown) having microprocessor (not shown) and a solid state memory (not shown). Initial values of trunk circumference and local temperature are entered into the data logger 24 via configuration files held within a SD (Secure Digital) card. After configuration, the data logger 24 operates autonomously for recording variations of the circumference values of the trunk 22. These values are recorded locally at the solid state memory, and transmitted wirelessly to a remote station via the antenna 78.

[Method of Configuring or Repairing]

Periodically, a technician, engineer or researcher visits the dendrometer 20, which is installed on to the trunk 22 in a remote forest. The technician firstly opens a cover (not shown) of the data logger 24 so that he replaces depleted lithium battery with a new fully-charged battery. Both external surfaces and internal electrical terminals of data logger 24 are cleaned for returning the data logger 24 back to the optimum condition. The dendrometer band 26 is also cleaned such that rust and debris are removed from exposed parts of the dendrometer band 26. Particularly, the plunger 40, the standard wiper 42 and contacting portion of the membrane potentiometer 50 are thoroughly cleaned, free from debris. The technician further cut off the riveted joint 39 that connects the circuit band 32 and the plunger band 34. An additional stainless band of similar width is provided for connecting the circuit band 32 and the plunger band 34 together. A suitable length of the additional stainless band is provided such that the standard wiper 42 will return to the beginning 10% portion of the membrane potentiometer 50 (collector and resistor). If necessary, the stainless spring 36 is replaced when hooking the circuit band 32 and the plunger band 34 together again. Other parts of the dendrometer 20 may also be replaced when necessary.

In the application, unless specified otherwise, the terms "comprising", "comprise", and grammatical variants thereof, intended to represent "open" or "inclusive" language such that they include recited elements but also permit inclusion of additional, non-explicitly recited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. The description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It will be apparent that various other modifications and adaptations of the application will be apparent to the person skilled in the art after reading the foregoing disclosure without departing from the spirit and scope of the application and it is intended that all such modifications and adaptations come within the scope of the appended claims.

REFERENCE NUMERALS 20 dendrometer
22 tree trunk
24 data logger
26 dendrometer band
28 cable
30 stainless belt
32 circuit band
34 plunger band
35 first end of the circuit band
36 spring
37 first end of the plunger band
38 stainless steel strip
39 first rivet
40 plunger
42 standard wiper
44 cylindrical casing
46 stainless steel ribbon
48 anchoring tag
50 membrane potentiometer
52 clip
54 connector
55 first wing
56 Pin A
57 second wing
58 Pin B
59 slit
60 Pin C
61 gap
62 microcontroller
63 plunger end
64 EEPROM
65 circuit end
67 end of the plunger band
68 thermistor
69 riveted tag
70 PC interface
72 Analog-to-Digital Converter
74 amplifier
76 potentiometer connector
78 antenna
201 sensor node
202 sensor node
203 sensor node
204 sensor node
205 sensor node
206 sensor node
207 sensor node
210 gateway node
212 base station

The invention claimed is:

1. Dendrometer comprising:
a dendrometer band that is flexible and extendable for encircling a tree trunk, and
an electronic component attached to the dendrometer band for moving together with the dendrometer band;
wherein the dendrometer band comprises a circuit band and a plunger band for carrying the electronic component, the circuit band and the plunger band being attached to each other and configured to cooperate with each other for providing telescopic motion in order to extend the dendrometer band in length directions of the circuit band and the plunger band, and
wherein length variation of the dendrometer band is configured to be converted to electronic signals by the electronic component.

2. Dendrometer of claim 1, wherein
the electronic component comprises a passive electronic component.

3. Dendrometer of claim 2, wherein
the passive electronic component comprises a potentiometer.

4. Dendrometer of claim 1, wherein
the circuit band, the plunger band or both comprise at least one stainless steel strip.

5. Dendrometer of claim 1, wherein
the plunger band comprises a stainless ribbon for mounting a plunger of the potentiometer.

6. Dendrometer of claim 1, wherein
the dendrometer band comprises a clip for guiding movement of the circuit band, the plunger band or both.

7. Dendrometer of claim 1, wherein
the dendrometer band comprises a stopper for limiting movement of the circuit band, the plunger band or both.

8. Dendrometer of claim 1, wherein
the dendrometer band further comprises a spring for connecting the circuit band and the plunger band.

9. Dendrometer of claim 1, wherein
the dendrometer band, the electronic component or both are weatherproof, scratchproof, dustproof, shockproof or a combination of any of these.

10. Dendrometer of claim 1, wherein
the dendrometer band, the electronic component or both are protected against intrusion of solid particles, liquid ingress, mechanical impact, electric shock or a combination of any of these.

11. Dendrometer of claim 1 further comprising:
a data logger that is connected to the electronic component for reading the electronic signals.

12. Dendrometer of claim 11 further comprising:
a cable for connecting the electronic component to the data logger.

13. Dendrometer of claim 12, wherein
the data logger comprises an electrical energy source for powering the data logger.

14. Dendrometer of claim 11, wherein
the data logger comprises an electrical energy source for powering the data logger.

15. Dendrometer of claim 11, wherein
the data logger further comprises a memory device for data storage.
16. Dendrometer of claim 11, wherein
the data logger further comprises an antenna for signal transmission or reception.
17. Dendrometer of claim 1, wherein
the dendrometer band, the electronic component or both comprises visible markings or inscriptions for visualizing the length variation.
18. Dendrometer of claim 1 further comprising:
a temperature sensor for correcting measurement error due to temperature variation.
19. Sensor Network comprising:
the dendrometer of claim 1, and
a gateway sensor node that is connected to the dendrometer.
20. Wireless Sensor Network comprising:
sensor network of claim 19, and
at least one radio transceiver having an aerial for providing communication between the dendrometer, the gateway sensor node or other computing devices.
21. Method for servicing the dendrometer according to claim 1 comprising:
cleaning a dendrometer band for giving sufficient range of longitudinal extension to the dendrometer band.
22. The method for servicing the dendrometer of claim 1, further comprising:
replacing faulty parts of the dendrometer band.
23. Method for using a dendrometer comprising:
clasping a flexible dendrometer band of the dendrometer onto a tree trunk such that the dendrometer can extend its length following circumference growth of the tree trunk,
providing a circuit band and a plunger band of the dendrometer band for carrying an electronic component of the dendrometer, the circuit band and the plunger band being attached to each other and configured to cooperate with each other for providing telescopic motion in order to extend the dendrometer band in length directions of the circuit band and the plunger band;
powering the dendrometer for generating electronic signals according length extension of the dendrometer, and
converting the electronic signals to circumference growth data of the tree trunk.
24. Method for claim 23 further comprising:
connecting an electronic component of the dendrometer to a data logger for data processing locally.
25. Method for claim 23 further comprising:
calculating the circumference growth data by compensating for thermal expansion of the dendrometer.
26. Method for claim 23 further comprising
transmitting the electronic signals to another electronic device.
27. Method for installing a dendrometer comprising:
providing a flexible dendrometer band having a circuit band, a plunger band and a clip for carrying an electronic component of the dendrometer and longitudinal extension of the circuit band, the plunger band or both,
encircling the dendrometer band around a tree trunk, and
joining the circuit band and the plunger band by a spring for clasping the tree trunk, and the circuit band and the plunger band being configured to cooperate with each other for providing telescopic motion in order to extend the dendrometer band in length directions of the circuit band and the plunger band.
28. Method for configuring a dendrometer comprising:
providing a circuit band and a plunger band for carrying an electronic component of a flexible dendrometer band,
examining range of relative movements between the circuit band and the plunger band,
adjusting lengths of the circuit band, the plunger band or both for providing telescopic motion and sufficient operation range to an electronic component of the dendrometer when clasping a tree trunk.
29. Method of claim 28 further comprising
compensating thermal expansion of the dendrometer.
30. Method of claim 29 further comprising:
connecting a data logger to the cable for receiving the electronic signals.
31. Method for making a dendrometer comprising:
providing a flexible dendrometer band that comprises a circuit band and a plunger band for carrying an electronic component of the dendrometer band, the circuit band and the plunger band being attached to each other and configured to cooperate with each other for providing telescopic motion in order to extend the dendrometer band in length directions of the circuit band and the plunger band,
attaching an electronic component to the dendrometer band for generating electronic signals when extending the dendrometer band, and
connecting leads of the electronic component to a cable for providing external access.

* * * * *